(12) United States Patent
Schnabel et al.

(10) Patent No.: US 11,291,404 B2
(45) Date of Patent: Apr. 5, 2022

(54) METHOD, SYSTEM AND COMPUTER READABLE STORAGE MEDIA FOR THE DETECTION OF ERRORS IN THREE-DIMENSIONAL MEASUREMENTS

(71) Applicant: DENTSPLY SIRONA INC., York, PA (US)

(72) Inventors: Ruwen Schnabel, Darmstadt (DE); Sascha Schneider, Mühltal (DE); Anders Adamson, Darmstadt (DE); Marcel Meyer, Bensheim (DE)

(73) Assignee: DENTSPLY SIRONA INC., York, PA (US)

( * ) Notice: Subject to any disclaimer, the term of this patent is extended or adjusted under 35 U.S.C. 154(b) by 139 days.

(21) Appl. No.: 16/579,995

(22) Filed: Sep. 24, 2019

(65) Prior Publication Data

US 2021/0085238 A1   Mar. 25, 2021

(51) Int. Cl.
| | | |
|---|---|---|
| *G06N 20/00* | (2019.01) | |
| *A61B 5/00* | (2006.01) | |
| *A61C 7/00* | (2006.01) | |
| *G06N 3/02* | (2006.01) | |
| *G06T 7/00* | (2017.01) | |

(52) U.S. Cl.
CPC ............ *A61B 5/4547* (2013.01); *A61C 7/002* (2013.01); *G06N 3/02* (2013.01); *G06N 20/00* (2019.01); *G06T 7/0012* (2013.01); *G06T 2207/30036* (2013.01)

(58) Field of Classification Search
CPC ........ A61B 5/4547; G06N 20/00; G06N 3/02; A61C 7/002; G06T 7/0012; G06T 2207/30036

USPC ........................................................ 382/128
See application file for complete search history.

(56) References Cited

U.S. PATENT DOCUMENTS

| | | | |
|---|---|---|---|
| 9,788,917 B2 | 10/2017 | Mah | |
| 2014/0272765 A1* | 9/2014 | Andreiko | A61B 1/00006 433/27 |
| 2018/0028294 A1 | 2/2018 | Azerinikov | |
| 2019/0026893 A1 | 1/2019 | Salah | |
| 2019/0269485 A1* | 9/2019 | Elbaz | A61B 1/00016 |
| 2021/0045858 A1* | 2/2021 | Salah | G16H 50/70 |
| 2021/0059796 A1* | 3/2021 | Weiss | G06N 3/08 |

FOREIGN PATENT DOCUMENTS

| | | |
|---|---|---|
| EP | 2018055145 A1 | 3/2018 |
| WO | 2014000745 A1 | 1/2014 |
| WO | 2019158442 A1 | 8/2019 |

OTHER PUBLICATIONS

"Recurrent Convolutional Neural Networks: A Better Model of Biological Object Recognition"; Courtney J. Spoerer at al; Frontiers in Psychology; Sep. 12, 2017.

(Continued)

*Primary Examiner* — Michael R Neff
(74) *Attorney, Agent, or Firm* — Dentsply Sirona Inc.

(57) ABSTRACT

A method, system and computer readable storage media for defects in images during three-dimensional measurement of teeth. An operator may use a dental camera to scan teeth and a trained deep neural network may automatically detect portions of the input images having defects and generate output information regarding those defects for corrective measures to be taken.

15 Claims, 11 Drawing Sheets

(56) References Cited

OTHER PUBLICATIONS

International Search Report; PCT/US2020/051930; Jan. 19, 2021 (completed); dated Jan. 22, 2021.
Written Opinion of the International Searching Authority; PCT/US2020/051930; Jan. 19, 2021 (completed); dated Jan. 22, 2021.

\* cited by examiner

METHOD, SYSTEM AND COMPUTER READABLE STORAGE MEDIA FOR THE DETECTION OF ERRORS IN THREE-DIMENSIONAL MEASUREMENTS

FIELD OF THE INVENTION

The present application relates generally to a method, a system and computer readable storage media for detecting errors in three-dimensional (3D) measurements and, more particularly, to a method, system and computer readable storage media for utilizing deep learning methods to detect errors in 3D measurements.

BACKGROUND OF THE INVENTION

Dental practitioners may be trained to detect errors in 3D images such as intraoral images using the naked eye. These errors may be defects/interferences in images caused by interference factors such as, for example, irregularities in intraoral scanner/camera's glass (e.g. scratches, fogging from breath, drops of saliva etc.), the presence of foreign objects (e.g. saliva bubbles or blood) on teeth being scanned, detrimental conditions in the measurement environment (e.g. sunlight or surgical light) as well as malfunctioning of the intraoral scanner (e.g. pixel faults in the camera's sensor). If the errors are not recognized during the measurement/scanning process, the measurement may not be completed, may have a low accuracy or may be noticeably delayed due to recurring interruptions.

However these errors as well as sources of the errors may be difficult to detect for both experienced and inexperienced dentists. Frequently, they may be noticed only at a later point in the measurement process or through conventional or manual checking of recording conditions. More specifically, some of the errors may be so subtle that conventional methods may not distinguish the errors from the general sensor noise and calibration errors, which may always be present (E.g. small scratches on camera glasses may cause small "bumps" in the measured data said "bumps" having heights similar to that of sensor noise. However, since the error is systematic, it may not always be averaged out by additional images. Other, more severe errors, may indeed cause conventional checking to recognize a problem and then stop the acquisition process. However, a conventional/manual method may not be able to diagnose the cause of the error and implementing filters with the required complexity using a conventional or manual approach is unmanageable.

An automatic detection of errors on the other hand may give an early indication of wrong measurements in order for suitable countermeasures to be taken.

U.S. Pat. No. 9,788,917B2 discloses a method for employing artificial intelligence in automated orthodontic diagnosis and treatment planning. The method may include providing an intraoral imager configured to be operated by a patient; receiving patient data regarding the orthodontic condition; accessing a database that comprises or has access to information derived from orthodontic treatments; generating an electronic model of the orthodontic condition; and instructing at least one computer program to analyze the patient data and identify at least one diagnosis and treatment regimen of the orthodontic condition based on the information derived from orthodontic treatments.

U.S. Patent Application Publication No. 20190026893A1 discloses a method for assessing the shape of an orthodontic aligner wherein an analysis image is submitted to a deep learning device, in order to determine a value of a tooth attribute relating to a tooth represented on the analysis image, and/or at least one value of an image attribute relating to the analysis image.

PCT Application PCT/EP2018/055145 discloses a method for constructing a restoration in which a dental situation is measured by means of a dental camera and a three-dimensional (3D) model of the dental situation is generated. A computer-assisted detection algorithm may then be applied to the 3D model of the dental situation and a type of restoration, a tooth number or a position of the restoration are automatically determined.

U.S. Application Publication No. 20180028294A1 discloses a method for Dental CAD Automation using deep learning. The method may include receiving a patient's scan data representing at least one portion of the patient's dentition data set; and identifying, using a trained deep neural network, one or more dental features in the patient's scan. Herein, design automation may be carried out after complete scans have been generated. However this method does not improve the actual scanning process.

SUMMARY OF THE INVENTION

Existing limitations associated with the foregoing, as well as other limitations, can be overcome by a method, system and computer readable storage media for utilizing deep learning methods to detect errors in 3D measurements. These 3D measurements may include intraoral measurements but may not be limited to such measurements. For example, extraoral measurements such as measurements on plaster models may be included.

In an aspect herein, the present invention may provide a computer implemented method for detecting defects during three-dimensional measurements, the method comprising: receiving, by one or more computing devices, individual images of a patient's dentition; automatically identifying said defects using one or more output label values of a trained deep neural network by segmenting the individual images of the patient's dentition into regions corresponding to semantic regions and/or error regions, determining one or more corrective regimens to correct the identified defects, and combining the individual images of the patient's dentition to form a corrected global 3D image. The output label values may be probability values.

In another aspect herein, the computer implemented method may further comprise one or more combinations of the following steps: (i) wherein the individual images are individual three-dimensional optical images, (ii) wherein the individual images are received as a temporal sequence of images, (iii) wherein the individual images comprise 3D measured data and color data of the patient's dentition, (iv) wherein an indication of a relevance of the identified error regions is based on corresponding semantic regions, (v) further comprising: training the deep neural network using the one or more computing devices and a plurality of individual training images, to map one or more defects in at least one portion of each training image to one or more probability values of a probability vector, wherein the training is done on a pixel level by classifying the individual training images and/or pixels of the individual training images into one or more classes corresponding to semantic data types and/or error data types, (vi) wherein the semantic data types are selected from the group consisting of teeth, cheek, lip, tongue, gingiva, filling and ceramic and wherein the error data types are selected from the group consisting of fogging, scratches, saliva droplets, dirt, blood, highlights, ambient lighting, measurement distance, pixel faults, (vii)

further comprising correcting the defects by masking out locations corresponding to the defects prior to registration of the individual images, (viii) further comprising correcting the defects by partially including contributions of the locations corresponding to the defects using predetermined weights, (ix) further comprising correcting the defects by automatically adjusting parameters of a dental camera corresponding to the defects, (x) wherein said parameters include exposure time, light intensity and temperature of the dental camera's glass, (xi) further comprising indicating the defects by relaying a warning to a user and/or generating a report concerning the error, (xii) wherein the deep neural network is a network chosen from the group consisting of Convolutional Neural Networks (CNN), Recurrent Neural Networks (RNN) and Recurrent Convolutional Neural Networks (Recurrent-CNN).

In yet another aspect of the present invention, a non-transitory computer-readable storage medium storing a program may be provided, which, when executed by a computer system, causes the computer system to perform a procedure comprising: receiving, by one or more computing devices, individual images of a patient's dentition; automatically identifying defects in said individual images of the patient's dentition using one or more output probability values of a trained deep neural network by segmenting the individual images of the patient's dentition into regions corresponding to semantic regions and/or error regions, determining one or more corrective regimens to correct the identified defects and combining the individual images of the patient's dentition to form a corrected global 3D image.

Further, an apparatus for detecting defects during three-dimensional measurement, may be provided, the apparatus comprising a processor configured to: receive, by one or more computing devices, individual images of a patient's dentition; automatically identify defects in said individual images of the patient's dentition using one or more output label values of a trained deep neural network by segmenting the individual images of the patient's dentition into regions corresponding to semantic regions and/or error regions, determine on or more corrective regimens to correct the identified defects and combine the individual images of the patient's dentition to form a corrected global 3D image.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein and wherein.

Figure 1:
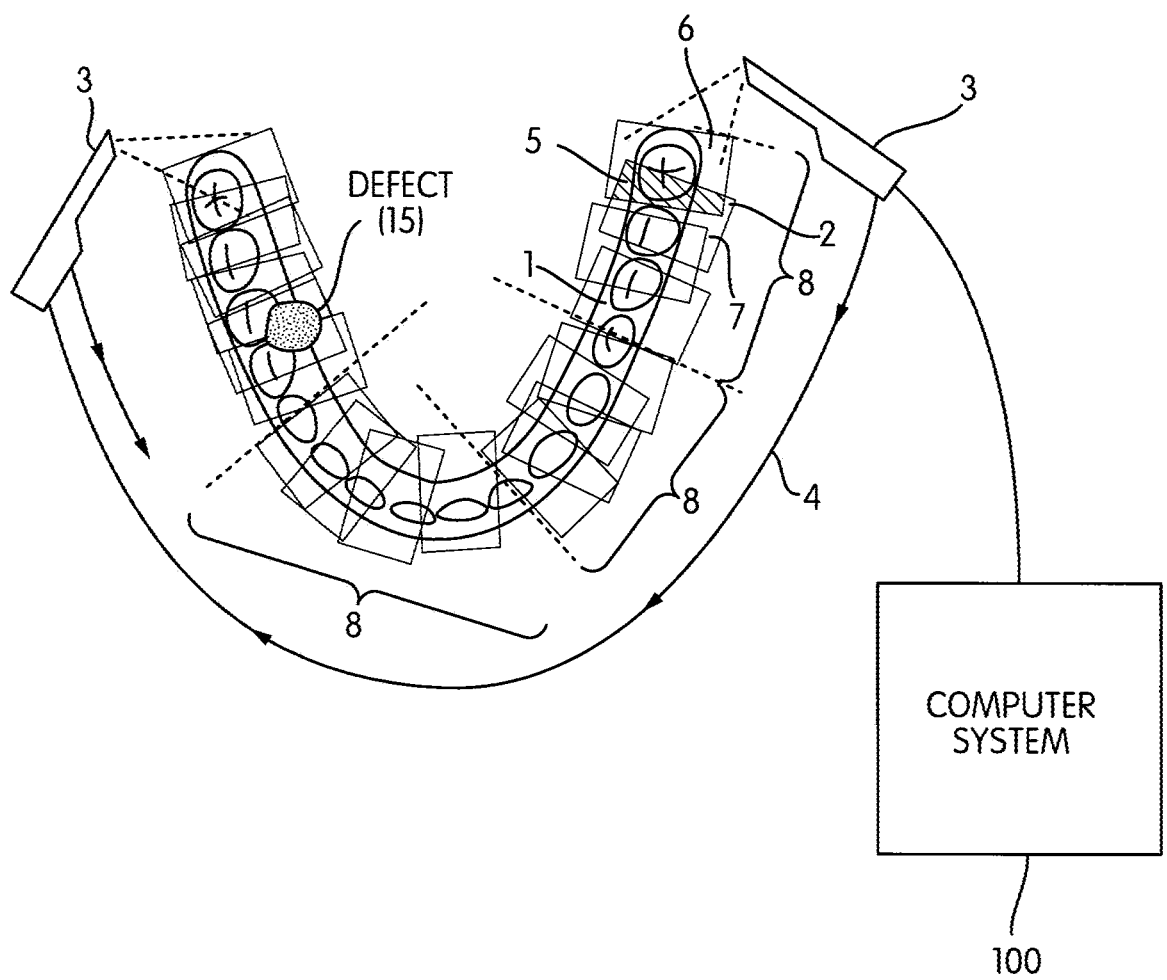
FIG. 1 is a sketch of a top view of an oral cavity illustrating the scanning/recording of individual images of a patient's dentition.

Different ones of the figures may have at least some reference numerals that may be the same in order to identify the same components, although a detailed description of each such component may not be provided below with respect to each Figure.

DETAILED DESCRIPTION OF THE INVENTION

In accordance with example aspects described herein, a method, system and computer readable storage media may be provided for utilizing deep learning methods to detect errors in 3D measurements.

System for Detecting Errors in 3D Measurements

The accurate 3D measurement of a patient's oral cavity may be hindered by factors such as saliva droplets, or blood on the patient's teeth. The system described herein may preferably obtain images, such as individual three-dimensional optical images 2 (FIG. 1), with each three-dimensional optical image 2 preferably comprising 3D measured data and color data of a measured surface of the teeth and preferably being recorded sequentially in an oral cavity through a direct intraoral scan. This may occur, for example, in a dental office or clinic and may be performed by a dentist or dental technician. The images may also be obtained indirectly through scanning an impression of the patient's teeth, or through a sequence of stored images. Using the images, preferably obtained in a temporal sequence, a computer-implemented system may automatically identify and/or correct errors/defects 15 in the images in order to facilitate accurate scanning of patient dentition. Herein, the correction may be done in real-time. Of course the images may also be individual two-dimensional (2D) images, RGB Images, Range-Images (two-and-a-half-dimensional, 2.5D), 4-Channel Images (RGB-D), where depth and color may not be in perfect alignment, i.e. depth and color images may be acquired at different time. periods.

Figure 3:
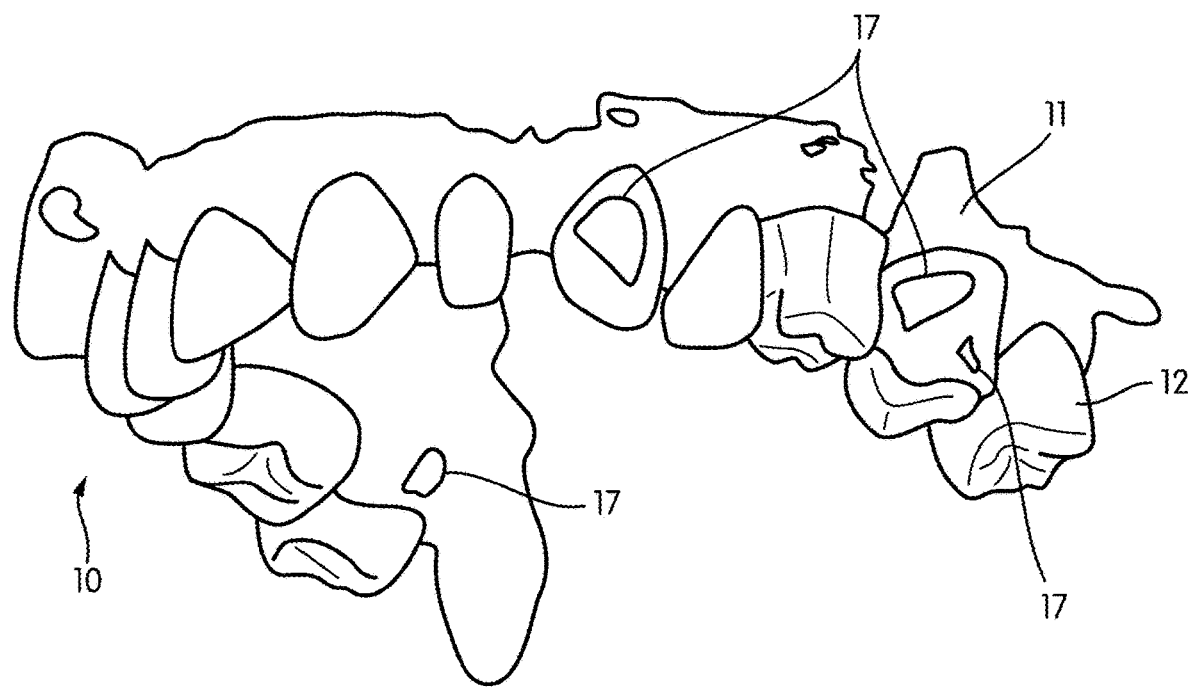
FIG. 3 is a perspective view of a global 3D image of a dentition formed from individual images with their defects not removed according to an embodiment of the present invention.

In the scanning process, a plurality of individual images may be created and then a sequence 8 of at least two individual images or a plurality of sequences 8 may be combined to form an overall/global 3D image 10 (FIG. 3). More specifically, as shown in FIG. 1, individual three-dimensional optical images 2, which are illustrated in the form of rectangles, may be obtained by means of a scanner/dental camera 3 which may be moved relative to the object 1 along a measurement path 4 during the measurement. The dental camera 3 may be a handheld camera, for example, which measures the object 1 using a fringe projection method. Other methods of 3D measurement may be realized by persons of ordinary skill in the art. An overlapping area 5 between a first image 6 and a second image 7, which is shown with a dashed line, is checked to determine if recording conditions are met by using a computer and if met, the three-dimensional optical images 2 may be combined to form a global 3D image 10. The recording conditions may include an adequate size, an adequate waviness, an adequate roughness, and/or an adequate number and arrangement of characteristic geometries. However, it may be difficult to program the computer to determine errors/defects 15 in the individual three-dimensional optical images 2 caused by interference factors in the same conventional way as the checking of the recording conditions. A neural network on the other hand may learn complex tasks to recognize the cause of errors 15 and either isolate affected regions (so that the scanning process can proceed without interruption) or give a diagnosis along with suggested measures for correction to the user. Said interference factors may include irregularities in intraoral scanner/camera's glass (e.g. scratches, fogging from breath, drops of saliva etc.), the presence of foreign objects (e.g. saliva bubbles, blood, dirt) on teeth being scanned, detrimental conditions in the measurement environment (e.g. sunlight or surgical light, measurement distance/angle from teeth) as well as malfunctioning of the intraoral scanner (e.g. pixel faults in the camera's sensor, faulty LED). Said interference factors may also be considered as errors/defects 15 themselves and may appear in the images. For example, defects 15 in the individual three-dimensional optical images 2 caused by blood (which may be similar to those caused by other fluids such as saliva droplets) may appear as highlights and reflections in the individual three-dimensional optical images 2, leading to errors in the measurement. The defects 15 caused by blood, for example, may be local to the regions covered by the blood. Thus, in removing the blood, the defects 15 may also be removed. Thus the terms defects 15 and errors may hereinafter be used to collectively refer to defects/errors/interferences/distortions and interference factors appearing in said individual three-dimensional optical images 2, which may at times be subtle enough to be missed by the naked eye and may result in the inaccurate measurement of patient dentition, time consuming measurement of patient dentition, due to the presence of a plurality of interruptions in the scanning process (thus requiring repositioning of the scanning device), and/or impossible measurement of the patient dentition (such as in the case of fogging of the camera glass).

Figure 4:
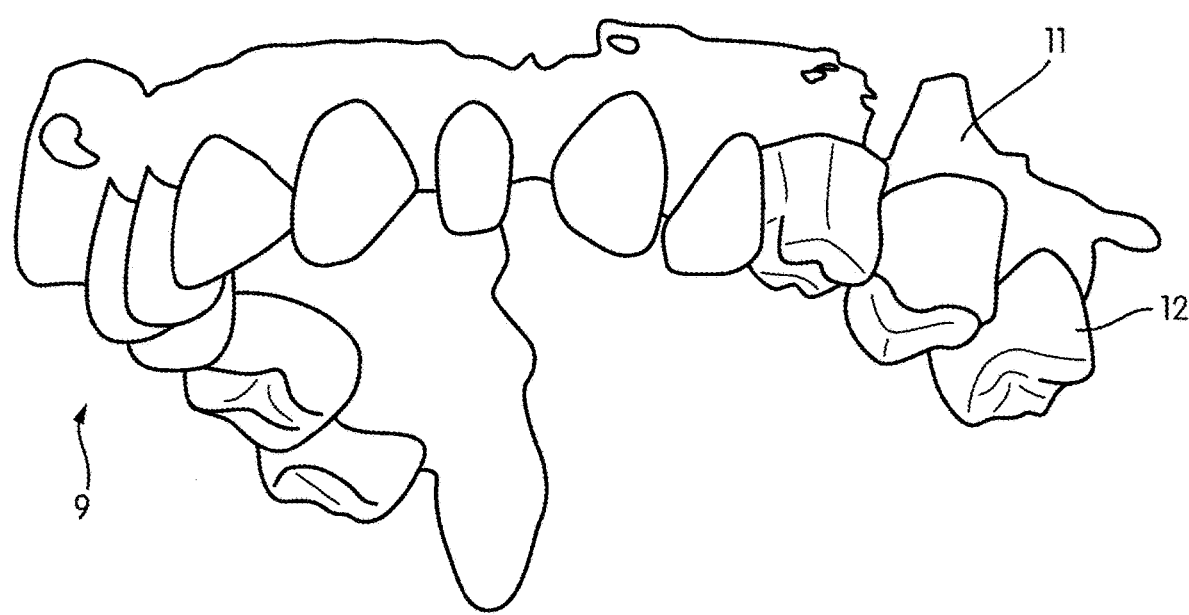
FIG. 4 is a perspective view of a corrected global 3D image of a dentition formed from individual images having their defects removed according to an embodiment of the present invention.

The system may therefore train neural networks such as deep neural networks, using a plurality of training data sets, to automatically recognize and/or correct errors/defects 15 in the three-dimensional optical images 2, preferably in real time. Therefore, global defects 17 propagated to the global 3D image 10 may be reduced or eliminated as shown in the corrected global 3D image 9 of FIG. 4 and/or the scan flow may be improved due to fewer/no interruptions. For example, the present system may detect and label defects 15 on a pixel level with labels that correspond to fogging, scratches, saliva droplets, dirt, blood, highlights etc. or on an image level with labels such as ambient lighting, measurement distance etc. The present system may also identify and label semantic data (for context purposes) with labels corresponding to teeth, cheek, lip, tongue, gingiva, filling, ceramic in the three-dimensional optical images 2. Moreover, the system may determine corrective measures and/or apply said determined corrective measures upon detecting the errors, the errors being preferably determined in a context aware manner (i.e. the context may be important to select an appropriate corrective method. E.g. saliva on cheek or gingiva may be ignored, since the required accuracy of parts of the scan corresponding to the cheek may be much lower than that of the teeth).

Figure 2:
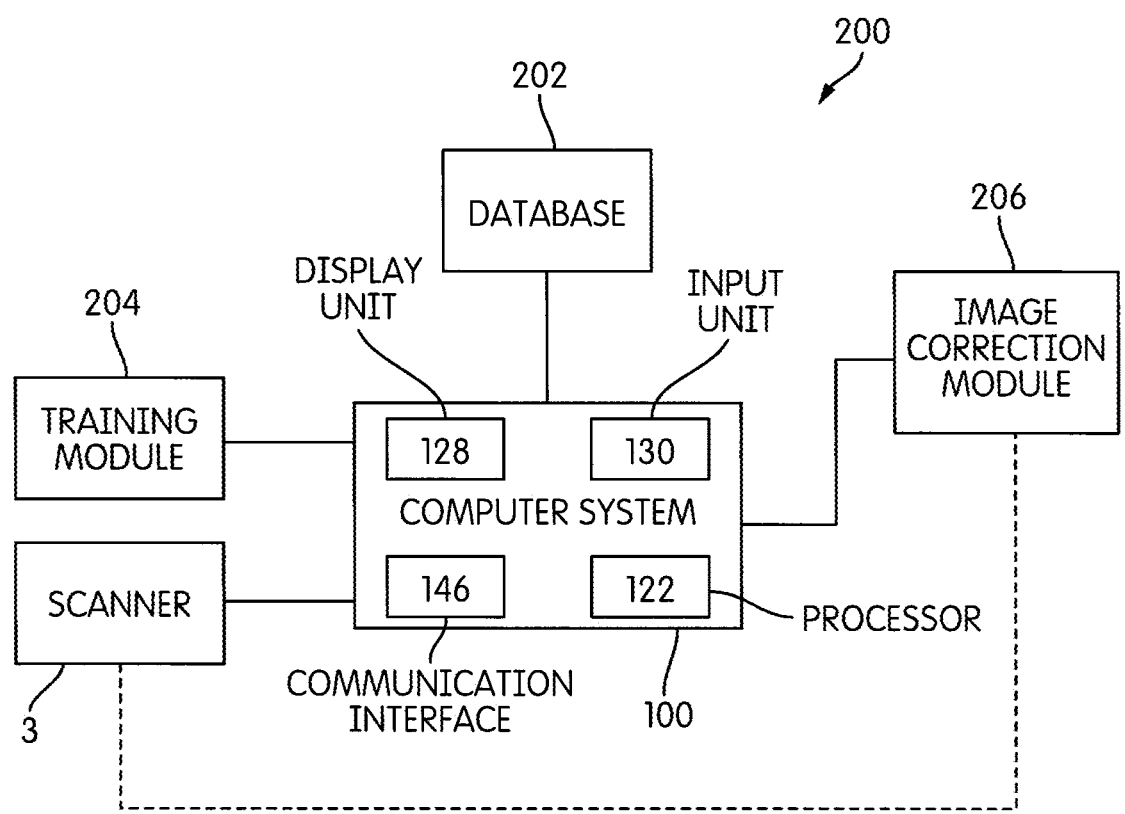
FIG. 2 is a high level block diagram of a system according to an embodiment of the present invention.

FIG. 2 shows a block diagram of a system 200 for recognizing dental information from individual three-dimensional optical images 2 of patients' dentitions according to one embodiment. System 200 may include a dental camera 3, a training module 204, an image correction module 206, a computer system 100 and a database 202. In another embodiment, the database 202, image correction module 206, and/or training module 204 may be part of the computer system 100 and/or may be able to directly and/or indirectly adjust parameters of the dental camera 3 based on a correction regimen. The computer system 100 may also include at least one computer processor 122, a user interface 126 and input unit 130. The computer processor may receive various requests and may load appropriate instructions, as stored on a storage device, into memory and then execute the loaded instructions. The computer system 100 may also include a communications interface 146 that enables software and data to be transferred between the computer system 100 and external devices.

The computer system 100 may receive error detection requests from an external device such as the dental camera 3 or a user (not shown) and may load appropriate instructions to detect said errors. Alternatively, the computer system may independently detect said errors upon receiving individual three-dimensional optical images 2, without waiting for a request.

In one embodiment, the computer system 100 may use many training data sets from a database 202 (which may include, for example, a plurality of individual three-dimensional optical images 2) to train one or more deep neural networks, which may be a part of training module 204. In some embodiments, system 200 may include a neural network module (not shown) that contains various deep learning neural networks such as Convolutional Neural Networks (CNN), Recurrent Neural Networks (RNN) and Recurrent Convolutional Neural Networks (Recurrent-CNN). An example Recurrent-CNN model is described in the publication by Courtney J. Spoerer et al, entitled "Recurrent Convolutional Neural Networks: A Better Model of Biological Object Recognition" Front. Psychol., 12 Sep. 2017, which is hereby incorporated by reference in its entirety, as if set forth fully herein.

The training data sets and/or inputs to the neural networks may be pre-processed. For example, in order to process color data in conjunction with 3D measurements a calibration may be applied to align color images with the 3D surface. Furthermore, standard data augmentation procedures such as synthetic rotations, scalings etc. may be applied to the training data sets and/or inputs.

The training module 204 may use training data sets with labels to supervise the learning process of the deep neural network. The labels may be used to describe a feature. The label values may be, for example, probability values of a probability vector. The training module 204 may conversely use unlabeled training data sets to train generative deep neural networks.

The training data sets may be designed to train one or more deep neural networks of training module 204 to identify the errors/defects 15. For example, to train a deep neural network to detect errors in the individual three-dimensional optical images 2 caused by saliva droplets, a plurality of real life individual three-dimensional optical image data sets, having defects 15 caused by saliva droplets may be used as the training data sets specifically for saliva droplets. In another example, to train the deep neural network to recognize semantic data (e.g., gingiva 11), another plurality of training data sets from real dental patients with one or more gingiva are selected to form a group of training data sets specifically for a gingiva. Database 202 may therefore contain different groups of training data sets, one group for each error data type and/or for each semantic data type, for example.

In an embodiment of the present invention, the training module 204 may train one or more deep neural networks in real-time. In some embodiments, training module 204 may pre-train one or more deep neural networks using training data sets from database 202 such that the computer system 100 may readily use one or more pre-trained deep neural networks to detect errors. It may then send information about the detected errors and or the individual three-dimensional optical images 2, preferably automatically and in real time, to an image correction module 206 for correction of the detected errors. The detected errors may be corrected using predetermined correction regimens described hereinafter and/or correction regimens obtained using artificial intelligence. For example, based on diagnostic data sets of past corrections with each diagnostic data set comprising detected errors, corresponding semantic data, corresponding corrections, as well as data from scientific literature, textbooks, input from users etc., the image correction module 206 may be adapted to identify, recommend and/or implement one or more correction regimens for the one or more detected errors. The correction regimen may include, for example, computing contributions to the final individual three-dimensional optical images coming from the sections having the errors, by using predetermined weights. Systems for employing artificial intelligence in dental planning are described in U.S. Pat. No. 9,788,917B2, entitled "Methods and systems for employing artificial intelligence in automated orthodontic diagnosis and treatment planning" which is hereby incorporated by reference in its entirety, as if set forth fully herein. Of course, other non-artificial intelligence correction regimens such as notifying a user, altering dental camera 3 parameters etc. may be employed.

The database 202 may also store data related to the deep neural networks and the identified errors along with corresponding individual three-dimensional optical images 2. Moreover, the computer system 100 may have a display unit 126 and input unit 130 with which a user may perform functions such as submitting a request and receiving and reviewing identified defects 15, etc. Other embodiments of the system 200 may include different and/or additional components. Moreover, the functions may be distributed among the components in a different manner than described herein.

Figure 5:
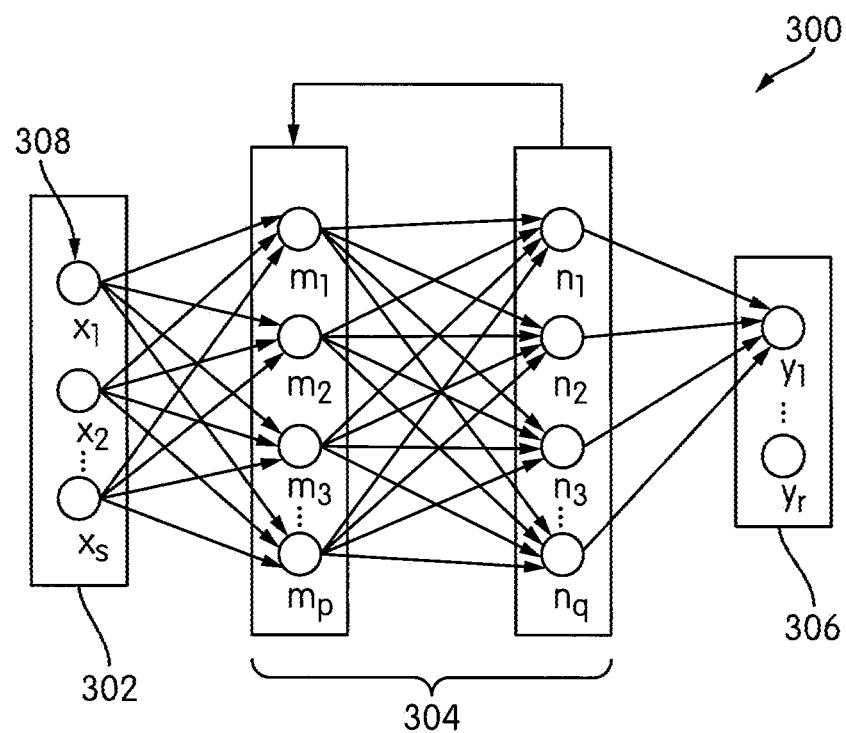
FIG. 5 is a high-level block diagram showing a structure of a neural network such as a deep neural network according to one embodiment.

FIG. 5 shows a block diagram illustrating a structure of a neural network such as a deep neural network 300 according to an embodiment of the present invention. It may have several layers including an input layer 302, one or more hidden layers 304 and an output layer 306. Each layer may consist of one or more nodes 308, indicated by small circles. Information may flow from the input layer 302 to the output layer 306, i.e. left to right direction, though in other embodiments, it may be from right to left, or both. For example, a recurrent network may take previously observed data into consideration when processing new data in a sequence 8 (e.g. current images may be segmented taking into consideration previous images), whereas a non-recurrent network may process new data in isolation. A node 308 may have an input and an output and the nodes of the input layer 308 may be passive, meaning they may not modify the data. For example, the nodes 308 of the input layer 302 may each receive a single value (e.g. a pixel value) on their input and duplicate the value to their multiple outputs. Conversely, the nodes of the hidden layers 304 and output layer 306 may be active, therefore being able to modify the data. In an example structure, each value from the input layer 302 may be duplicated and sent to all of the hidden nodes. The values entering the hidden nodes may be multiplied by weights, which may be a set of predetermined numbers associated with each of the hidden nodes. The weighted inputs may then be summed to produce a single number.

In an embodiment according to the present invention, the deep neural network 300 may use pixels of the individual three-dimensional optical images 2 as input when detecting some defects 15 such as fogging, scratches, saliva droplets, dirt, blood, highlights etc. The individual three-dimensional optical images 2 may be color images. Herein, the number of nodes in the input layer 302 may be equal to the number of pixels in an individual three-dimensional optical image 2. In an example embodiment, one neural network may be used for all defects 15 and in another embodiment, different networks may be used for different defects 15. In another example, the deep neural network 300 may classify the individual three-dimensional optical images 2 instead of individual pixels when detecting some defects 15 such as those caused by ambient light and measurement distance. In a further embodiment, the inputs may be subsampled inputs, such as every $4^{th}$ pixel. In yet another embodiment, the deep neural network may have as inputs a plurality of data acquired by the dental camera 3 such as color-images, depth measurements, accelerations as well as device parameters such as exposure times, aperture etc. It may also incorporate a temporal sequence of the acquired data such as through employing a Recurrent Convolutional Neural Network (since some defects 15 may be difficult to detect using a single image). Defects 15 may in some cases be visible mostly from a characteristic distortion that stays at the same image locations while the teeth are changing from image to image. This applies to interference factors such as fogging, for example, as well as to scratches to a lesser extent. A recurrent network may be well suited to recognize such features in an image sequence 8. The deep neural network may output labels which may be, for example, a probability vector that includes one or more probability values of each pixel input belonging to certain categories. For example, the output may contain a probability vector containing probability values wherein the highest probability values may define the defects 15. The deep neural network may also output a map of label values without any attached probabilities. Moreover different classifications may be achieved. For example, a first classification may include one or more of defect categories, e.g., scratches, fogging from breath, saliva bubbles, blood, dirt, sunlight, surgical light, measurement distance from teeth, pixel faults in the camera's sensor etc. Another classification may include one or more of semantic categories e.g. teeth, cheek, lip, tongue, gingiva, filling, ceramic etc. A deep neural network can be created for each classification.

As discussed, the deep neural network may be a Convolutional Neural Network (CNN), a Recurrent Neural Network (RNN), a Recurrent Convolutional Neural Network (Recurrent-CNN) or the like.

Method for Detecting Errors in 3D Measurements

Figure 6A:
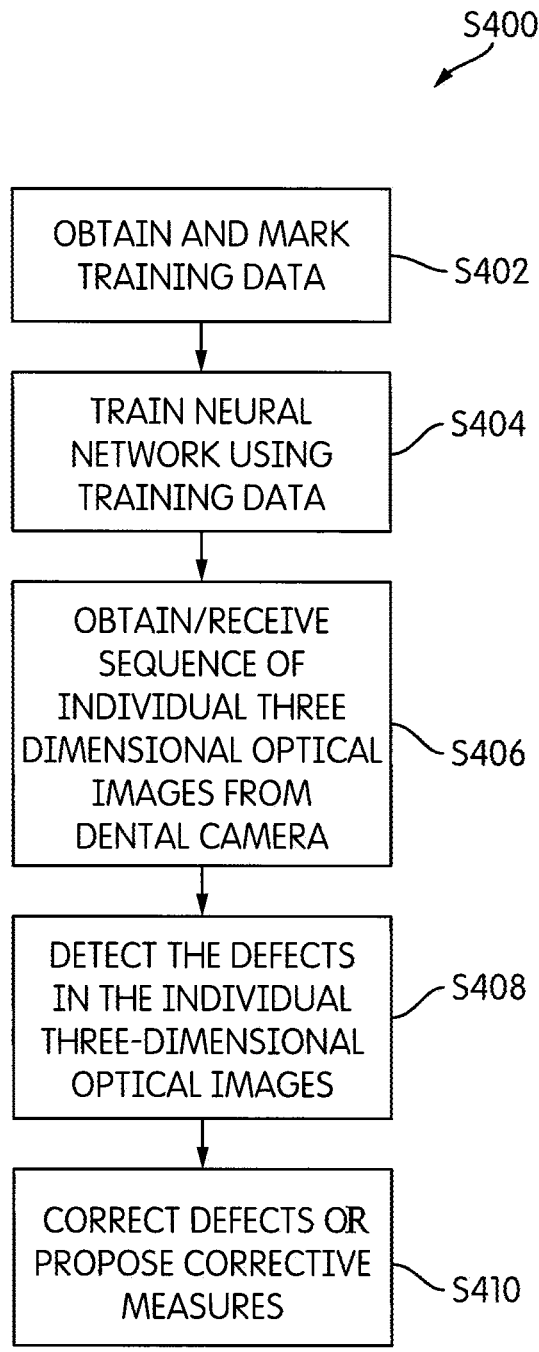
FIG. 6A is a flow chart illustrating a method according to an embodiment of the present invention.

Having described the system 200 of FIG. 2 reference will now be made to FIG. 6A, which shows a process S400 in accordance with at least some of the example embodiments herein.

Figure 6B:
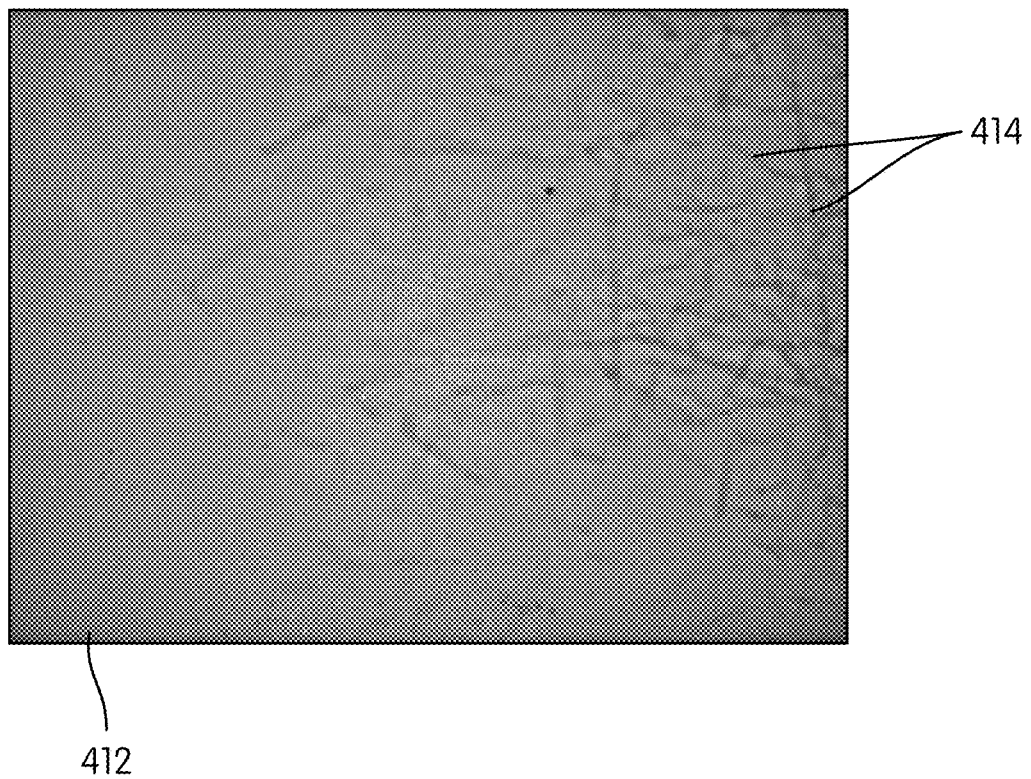
FIG. 6B is a sample image for training according to an embodiment of the present invention.

The process S400 may begin by obtaining and marking areas of interest in the training data sets with predetermined labels, Step S402. For example, sample defects 414 on sample image 412 (said sample image 414 taken in a dark room and which would be black were there no interference factors) shown in FIG. 6B may be labelled as scratches. The marking of the training images may be done digitally e.g. by setting dots on the images corresponding to the points of interest.

The training data may be labeled in order to assign semantics to the individual three-dimensional optical images 2. This may happen on a per-pixel level for color or depth information. Alternatively, meshes of complete 3D-models may be cut to compute corresponding per-pixel labels for single images. Moreover said meshes may be segmented such that the labeling process may be automated. The meshes may be labelled and the labels may be transferred to corresponding pixels of the single images in order to reduce the amount of work needed to label. These labels may distinguish between teeth, cheek, lip, tongue, gingiva, filling, ceramic while assigning no label to anything else. Irrelevant for the measurement may be cheek, lip, tongue and unlabeled data.

The training data may also be labeled in order to assign defect labels to the individual three-dimensional optical images 2. This may also be done on a per-pixel level for image or depth information. For example, the training data may be labeled on a pixel level for fogging, scratches, saliva droplets, dirt, blood, highlights and on an image level for other information such as ambient lighting, measurement distance, aperture etc.

The semantic labels may overlap with markers for defects 15, e.g. labels such as "Tooth+Saliva", "Tooth+Blood", "Tooth+Scratch" and "Tooth" may be achieved, and these labels may be distinguishable from other labels such as "Cheek+Scratch", i.e. saliva droplets on teeth (which may be a relevant defect) may be distinguished from saliva droplets on the cheek (which may be an irrelevant defect). This way, false notifications may be avoided.

In an embodiment, certain efficiently computable filters such as image processing filters including cross correlation, optical flow, edge detectors, difference images and moving averages, may be applied to the input data and the resulting filtered images with the same or lower pixel resolution fed into the deep neural network 300 as additional input, in order to optimize the computational effort and increase network practicability. The neural network's input layer may contain additional nodes in order process the additional per-pixel information from the image filters.

Using this set of labeled or classified images, a deep neural network 300 may be built and fed with the labeled images allowing the network to "learn" from it such that the network may produce a network wiring that may segment new images on its own.

As another option to segmentation on a per-image basis or on a per-pixel basis, segmentation may involve classification on a level slightly higher than a per-pixel level (on a per "super-pixel" level, i.e. "super-pixels" are parts of images that are larger than normal pixels of the image).

Instructions and algorithms of process S400 may be stored in a memory of the computer system 100 and may be loaded and executed by processor 122 to train (Step S404) one or more deep neural networks using the training data sets to detect one or more defects 15 based on one or more output probability values of a probability vector. For example, if one of the probability values of the probability vector that corresponds to ambient light is 90%, then the neural network may detect excessive ambient light as one of the defects 15 in the individual three-dimensional image. In another example, if a probability value corresponding to a location of scratches is high, then the neural network identifies that corresponding location as the location of the scratches. Therefore, a deep neural network may be built and fed with the labeled images allowing the network to "learn" from it such that the network may produce a network wiring that may segment new images on its own.

The training may be done once, a plurality of times or intermittently. The training may also be semi- or self-supervised. For example, after a first training, the deep neural network may receive or obtain previously unseen images and the output may be obtained, and corresponding feedback may be given such that the network may preferably operate on its own eventually to classify images without human help. This may be done on a pixel level or on an image level. For example, on an image level, the deep neural network 300 may be trained to map the images having ambient light and images having no ambient light to probability vectors that have probability values indicating the probabilities that the images have ambient light. The probability value indicating that the images have ambient light may therefore be the highest in the vectors. Therefore, the deep neural network 300 may be trained such that when a sequence 8 of individual three-dimensional optical images 2 are input into the deep neural network 300, the deep neural network may return resulting probability vectors for each image indicating the category (having ambient light or not) in which the images belongs.

After the training, the deep neural network may obtain or receive a sequence 8 of individual three-dimensional optical images from a dental camera 3 to segment in real time (Step S406) and may detect the defects 15 in the images (Step S408). Upon detecting said defects 15, the correction module 206 may correct (Step S410) the defects 15 and/or propose corrective measures. This may be done in real time in sequential image registration (of the individual three-dimensional optical images) or in subsequent processing steps such as in global image registration (registration of all acquired images simultaneously 8), model surface reconstruction and/or model texture generation. Correction may be done by masking out unreliable data points corresponding to the defect locations and/or using the data with lower weights so as to allow unaffected data points to override the errors introduced by the interference factors.

Figure 7:
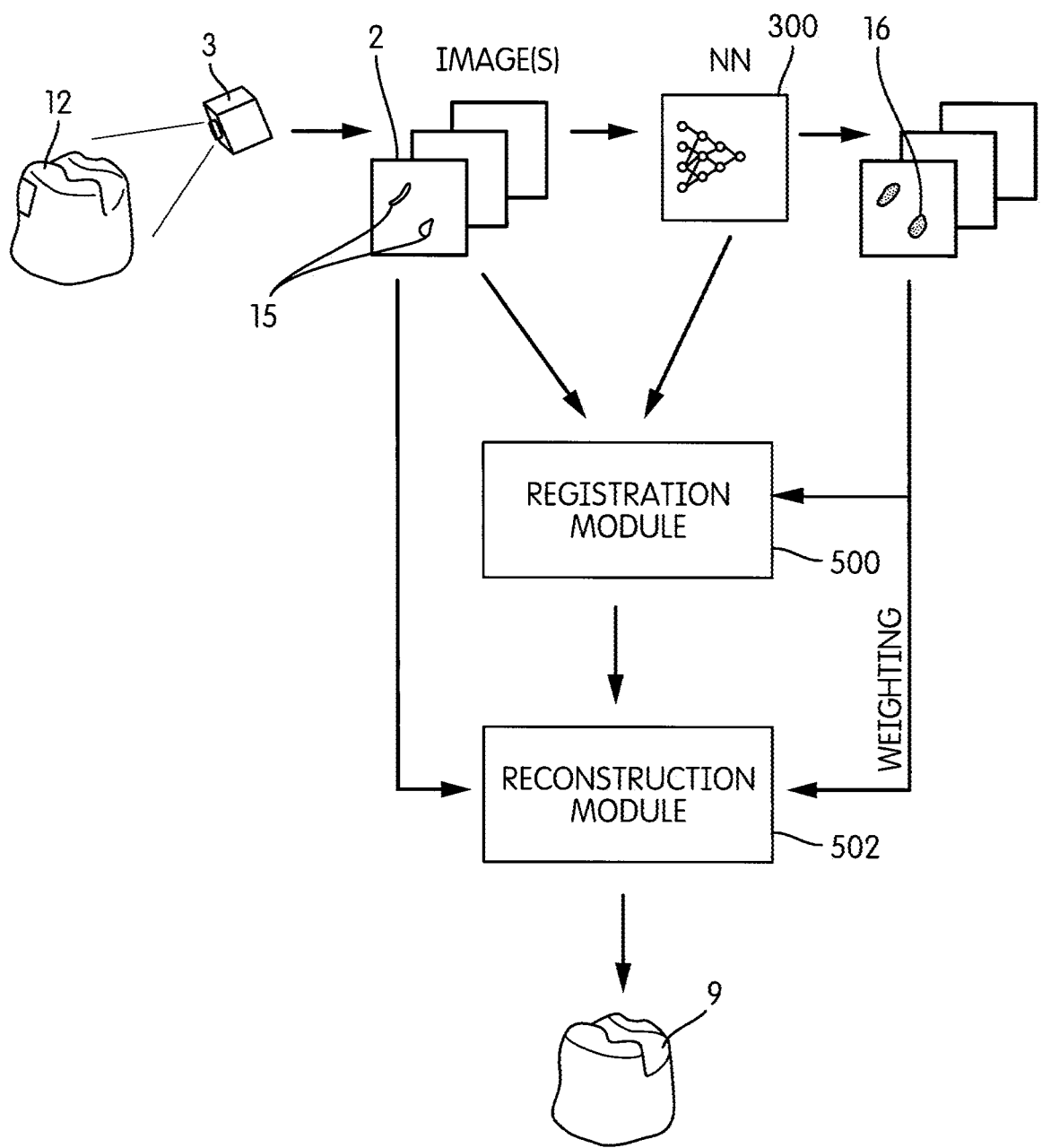
FIG. 7 is a block diagram illustrating an embodiment of the present invention.

FIG. 7 shows an embodiment of the present invention wherein the dental camera 3 records teeth 12 intraorally and generates a sequence 8 of images which include defects 15. The sequence 18 of images is input into the deep neural network 300 which then detects the defects 15 and labels the locations 16 corresponding to the defects 15. In a next step, the locations 16 are preferably ignored by masking them out prior to registration of the images using a registration module 500. In another step, a fully reconstructed triangle mesh/fully reconstructed 3D image/corrected global 3D image 9 may be obtained from the masked images using a reconstruction module 502. Said reconstruction module 502 may also be used to generate the fully reconstructed triangle mesh 9 by partially including contributions from the locations 16 corresponding to the defects 15 through weighting means using predetermined weights. Said reconstruction module may also be used to generate a colored texture for the reconstructed triangle mesh 9 using the same weighting mechanism.

Figure 8:
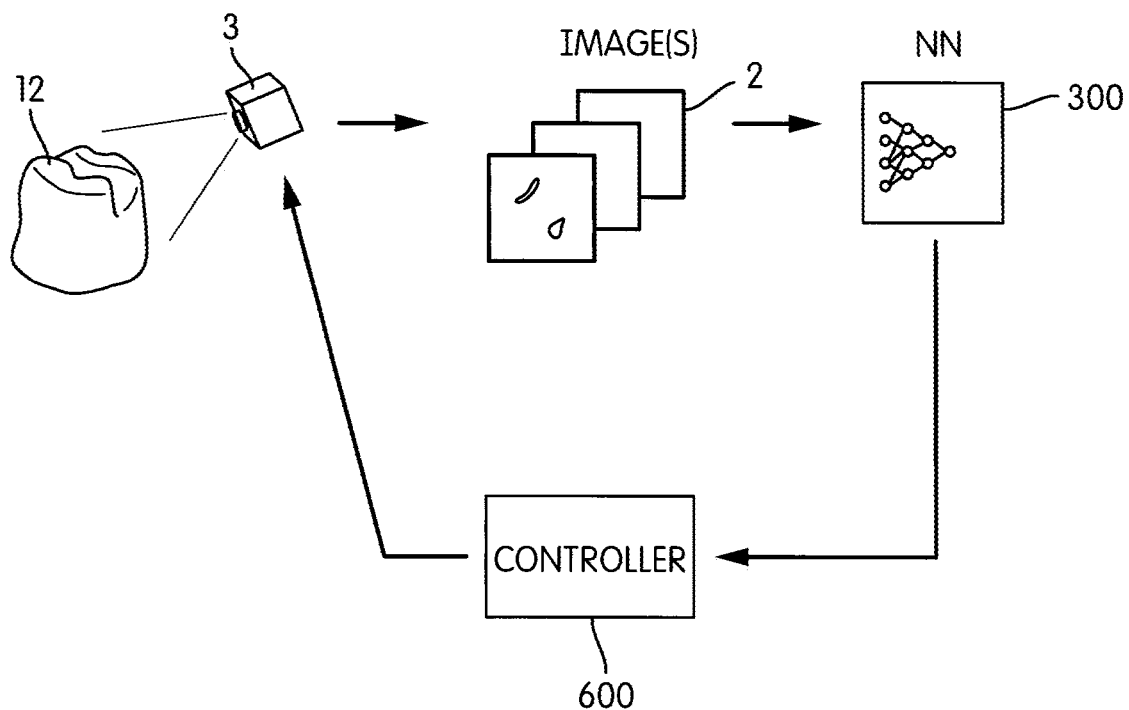
FIG. 8 is another block diagram illustrating another embodiment of the present invention.

FIG. 8 shows another embodiment of the present invention, wherein the deep neural network outputs information (such as a binary image showing locations 16 of defects 15, or an indication of corrective measures to be taken) or otherwise information such that said information is used by a controller 600 to automatically adjust parameters of the dental camera corresponding to the detected defects 15 in order to reduce or eliminate future/incoming defects 15, e.g. based on the output, exposure time or light intensity of the dental camera 3 may be automatically increased or decreased and/or the camera's glass (or mirror, in some cases) may be heated to reduce/remove fogging. In an embodiment herein, the extent of the adjustment may be based on the relevance and/or size/amount of the defect 15.

Figure 9:
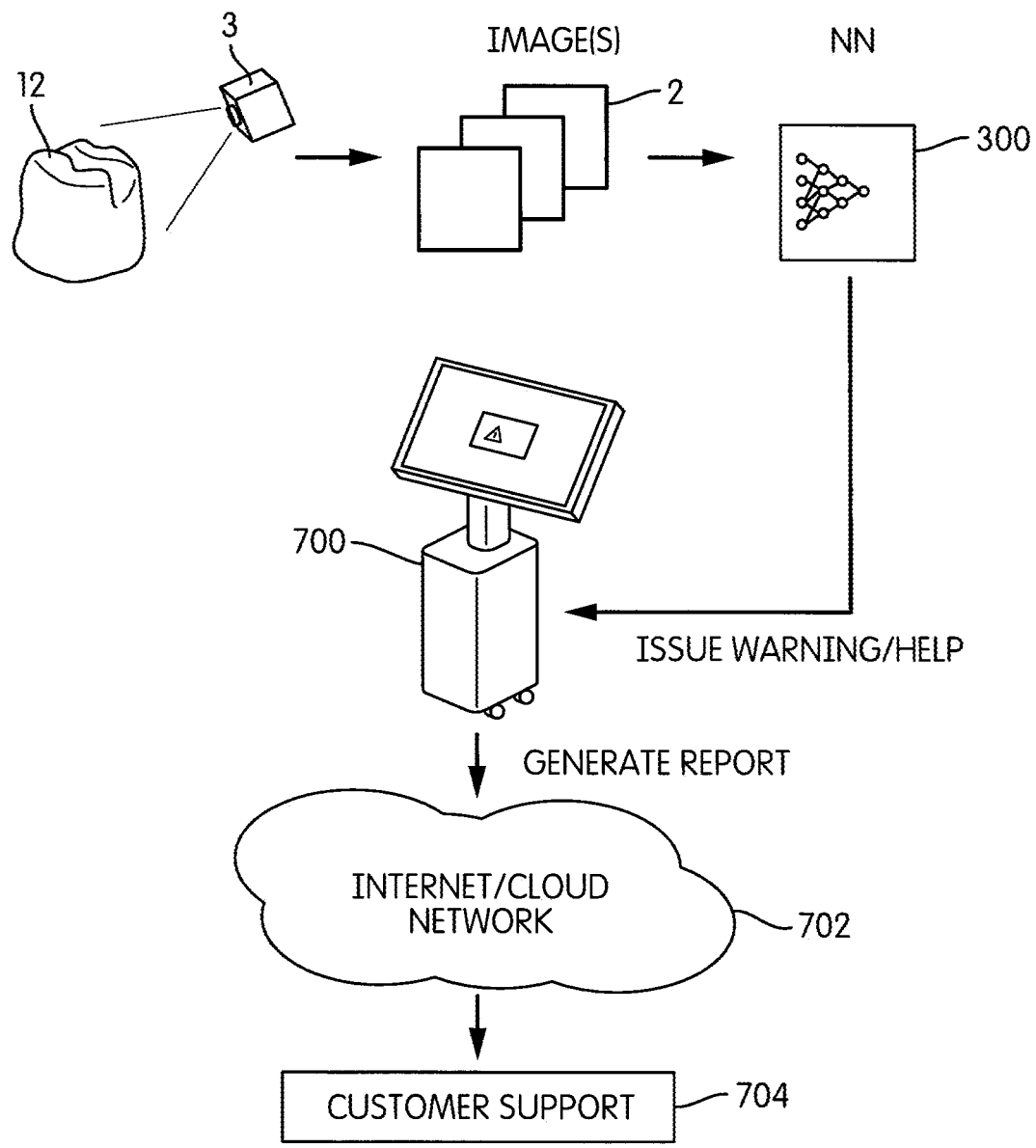
FIG. 9 is yet another block diagram illustrating an embodiment of the present invention.

FIG. 9 shows yet another embodiment of the present invention, wherein the deep neural network 300 issues information concerning a warning to the user. The warning may be propagated to an acquisition unit 700 which may generate a report that may be accessed by a client such as customer support via a network 702 such as a cloud network or internet, in order to take corrective actions.

Computer System for Detecting Errors in 3D Measurements

Figure 10:
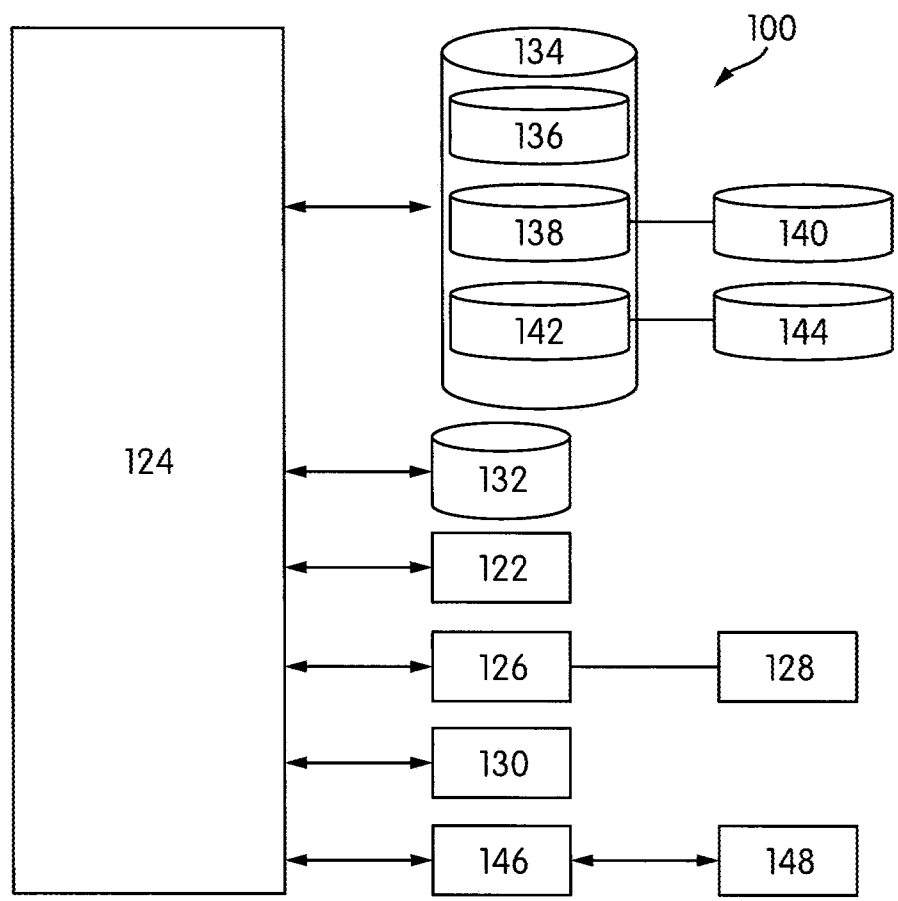
FIG. 10 is a block diagram showing a computer system according to an exemplary embodiment of the present invention.

Having described the process S400 of FIG. 6A reference will now be made to FIG. 10, which shows a block diagram of a computer system 100 that may be employed in accordance with at least some of the example embodiments herein. Although various embodiments may be described herein in terms of this exemplary computer system 100, after reading this description, it may become apparent to a person skilled in the relevant art(s) how to implement the invention using other computer systems and/or architectures.

The computer system 100 may include or be separate from the training module 204, database 202 and/or image correction module 206. The modules may be implemented in hardware, firmware, and/or software. The computer system may also include at least one computer processor 122, user interface 126 and input unit 130. The input unit 130 in one exemplary embodiment may be used by the dentist along with a display unit 128 such as a monitor to send instructions or requests about detecting defects 15. In another exemplary embodiment herein, the input unit 130 is a finger or stylus to be used on a touchscreen interface (not shown). The input unit 130 may alternatively be a gesture/voice recognition device, a trackball, a mouse or other input device such as a keyboard or stylus. In one example, the display unit 128, the input unit 130, and the computer processor 122 may collectively form the user interface 126.

The computer processor 122 may include, for example, a central processing unit, a multiple processing unit, an application-specific integrated circuit ("ASIC"), a field programmable gate array ("FPGA"), or the like. The processor 122 may be connected to a communication infrastructure 124 (e.g., a communications bus, or a network). In an embodiment herein, the processor 122 may receive a request for 3D measurement and may automatically detect defects 15 in the images, automatically correct said defects 15 in the images using the training module 204, database 202 and image correction module 206. The processor 122 may achieve this by loading corresponding instructions stored in a non-transitory storage device in the form of computer-readable program instructions and executing the loaded instructions.

The computer system 100 may further comprise a main memory 132, which may be a random access memory ("RAM") and also may include a secondary memory 134. The secondary memory 134 may include, for example, a hard disk drive 136 and/or a removable-storage drive 138. The removable-storage drive 138 may read from and/or write to a removable storage unit 140 in a well-known manner. The removable storage unit 140 may be, for example, a floppy disk, a magnetic tape, an optical disk, a flash memory device, and the like, which may be written to and read from by the removable-storage drive 138. The removable storage unit 140 may include a non-transitory computer-readable storage medium storing computer-executable software instructions and/or data.

In further alternative embodiments, the secondary memory 134 may include other computer-readable media storing computer-executable programs or other instructions to be loaded into the computer system 100. Such devices may include a removable storage unit 144 and an interface 142 (e.g., a program cartridge and a cartridge interface); a removable memory chip (e.g., an erasable programmable read-only memory ("EPROM") or a programmable read-only memory ("PROM")) and an associated memory socket; and other removable storage units 144 and interfaces 142 that allow software and data to be transferred from the removable storage unit 144 to other parts of the computer system 100.

The computer system 100 also may include a communications interface 146 that enables software and data to be transferred between the computer system 100 and external devices. Such an interface may include a modem, a network interface (e.g., an Ethernet card, a wireless interface, ac loud delivering hosted services over the internet, etc.), a communications port (e.g., a Universal Serial Bus ("USB") port or a FireWire® port), a Personal Computer Memory Card International Association ("PCMCIA") interface, Bluetooth®, and the like. Software and data transferred via the communications interface 146 may be in the form of signals, which may be electronic, electromagnetic, optical or another type of signal that may be capable of being transmitted and/or received by the communications interface 146. Signals may be provided to the communications interface 146 via a communications path 148 (e.g., a channel). The communications path 148 may carry signals and may be implemented using wire or cable, fiber optics, a telephone line, a cellular link, a radio-frequency ("RF") link, or the like. The communications interface 146 may be used to transfer software or data or other information between the computer system 100 and a remote server or cloud-based storage.

One or more computer programs or computer control logic may be stored in the main memory 132 and/or the secondary memory 134. The computer programs may also be received via the communications interface 146. The computer programs may include computer-executable instructions which, when executed by the computer processor 122, cause the computer system 100 to perform the methods as described herein.

In another embodiment, the software may be stored in a non-transitory computer-readable storage medium and loaded into the main memory 132 and/or the secondary memory 134 of the computer system 100 using the removable-storage drive 138, the hard disk drive 136, and/or the communications interface 146. Control logic (software), when executed by the processor 122, causes the computer system 100, and more generally the system for detecting scan interferences, to perform all or some of the methods described herein.

Implementation of other hardware and software arrangement so as to perform the functions described herein will be apparent to persons skilled in the relevant art(s) in view of this description.

What is claimed is:

1. A method comprising:
   receiving, by one or more computing devices, individual images of a patient's dentition as a temporal sequence;
   providing the individual images as input to a trained deep neural network;
   automatically identifying in the individual images defects due to one or more interference factors using one or more output label values of the trained deep neural network, said defects being characteristic of inaccurate measurement of patient dentition, time consuming measurement of patient dentition relative to a measurement without said defects and/or impossible measurement of patient dentition, said automatically identifying being performed by the trained neural network segmenting the individual images of the patient's dentition into regions corresponding to semantic regions and/or error regions, determining one or more corrective regimens to correct the automatically identified defects in a context aware manner, an indication of a relevance of the error regions for the context aware manner being based on corresponding semantic regions;

correcting said automatically identified defects in said context aware manner; and combining, responsive to said correcting, the individual images of the patient's dentition to form a corrected global 3D image.

2. The method according to claim 1, wherein the individual images are individual three-dimensional optical images.

3. The method according to claim 1, wherein the individual images comprise 3D measured data and color data of the patient's dentition.

4. The method according to claim 1, further comprising: training the deep neural network using the one or more computing devices and a plurality of individual training images, to map one or more defects in at least one portion of each training image to one or more label values, wherein the training is done on a pixel level by classifying the individual training images and/or pixels of the individual training images into one or more classes corresponding to semantic data types and/or error data types.

5. The method according to claim 4, wherein the semantic data types are selected from the group consisting of teeth, cheek, lip, tongue, gingiva, filling and ceramic and wherein the error data types are selected from the group consisting of fogging, scratches, saliva droplets, dirt, blood, highlights, ambient lighting, measurement distance, pixel faults.

6. The method according to claim 1, further comprising correcting the defects by masking out locations corresponding to the defects prior to registration of the individual images.

7. The method according to claim 1, further comprising correcting the defects by partially including contributions of the locations corresponding to the defects using predetermined weights.

8. The method according to claim 1, further comprising correcting the defects by automatically adjusting parameters of a dental camera corresponding to the defects.

9. The method according to claim 8, wherein said parameters include exposure time, light intensity and temperature of the dental camera's glass.

10. The method according to claim 1, further comprising indicating the defects by relaying a warning to a user and/or generating a report concerning the error.

11. The method according to claim 1, wherein the deep neural network is a network chosen from the group consisting of Convolutional Neural Networks (CNN), Recurrent Neural Networks (RNN) and Recurrent Convolutional Neural Networks (Recurrent-CNN).

12. The method according to claim 1, wherein the individual images are individual two-dimensional (2D) images.

13. A non-transitory computer-readable storage medium storing a program which, when executed by a computer system, causes the computer system to perform a procedure comprising:

receiving, by one or more computing devices, individual images of a patient's dentition as a temporal sequence;

providing the individual images as input to a trained deep neural network;

automatically identifying in the individual images defects due to one or more interference factors using one or more output label values of the trained deep neural network, said defects being characteristic of inaccurate measurement of patient dentition, time consuming measurement of patient dentition relative to a measurement without said defects and/or impossible measurement of patient dentition, said automatically identifying being performed by the trained neural network segmenting the individual images of the patient's dentition into regions corresponding to semantic regions and/or error regions, determining one or more corrective regimens to correct the automatically identified defects in a context aware manner, an indication of a relevance of the error regions for the context aware manner being based on corresponding semantic regions;

correcting said automatically identified defects in said context aware manner; and combining, responsive to said correcting, the individual images of the patient's dentition to form a corrected global 3D image.

14. A system for detecting defects during three-dimensional measurement, comprising a processor configured to perform the steps comprising:

receiving, by one or more computing devices individual images of a patient's dentition as a temporal sequence;

providing the individual images as input to a trained deep neural network;

automatically identifying in the individual images defects due to one or more interference factors using one or more output label values of the trained deep neural network, said defects being characteristic of inaccurate measurement of patient dentition, time consuming measurement of patient dentition relative to a measurement without said defects and/or impossible measurement of patient dentition, said automatically identifying being performed by the trained neural network segmenting the individual images of the patient's dentition into regions corresponding to semantic regions and/or error regions, determining one or more corrective regimens to correct the automatically identified defects in a context aware manner, an indication of a relevance of the error regions for the context aware manner being based on corresponding semantic regions;

correcting said automatically identified defects in said context aware manner; and combining, responsive to said correcting, the individual images of the patient's dentition to form a corrected global 3D image.

15. The system according to claim 14, wherein the deep neural network is a network chosen from the group consisting of Convolutional Neural Networks (CNN), Recurrent Neural Networks (RNN) and Recurrent Convolutional Neural Networks (Recurrent-CNN).

* * * * *